(12) United States Patent
Betts et al.

(10) Patent No.: US 8,103,356 B2
(45) Date of Patent: Jan. 24, 2012

(54) HIGH FREQUENCY EPIDURAL NEUROMODULATION CATHETER WITHOUT NEEDLE FOR EFFECTUATING RF TREATMENT

(75) Inventors: Andres Betts, San Clemente, CA (US); Shiva Sharareh, Laguna Niguel, CA (US)

(73) Assignee: Vertech, Inc., San Clemente, CA (US)

( * ) Notice: Subject to any disclaimer, the term of this patent is extended or adjusted under 35 U.S.C. 154(b) by 487 days.

(21) Appl. No.: 12/359,204

(22) Filed: Jan. 23, 2009

(65) Prior Publication Data

US 2009/0163850 A1 Jun. 25, 2009

Related U.S. Application Data

(63) Continuation-in-part of application No. 11/752,210, filed on May 22, 2007, now Pat. No. 8,075,556.

(60) Provisional application No. 60/802,685, filed on May 23, 2006.

(51) Int. Cl.
*A61F 2/00* (2006.01)
(52) U.S. Cl. ...................................... 607/101
(58) Field of Classification Search ............... 604/22; 606/33, 38–41; 607/101, 102, 154, 156
See application file for complete search history.

(56) References Cited

U.S. PATENT DOCUMENTS

| | | | | |
|---|---|---|---|---|
| 5,122,137 A | * | 6/1992 | Lennox | 606/40 |
| 5,421,819 A | * | 6/1995 | Edwards et al. | 604/22 |
| 5,433,739 A | | 7/1995 | Sluijter et al. | |
| 5,902,251 A | * | 5/1999 | vanHooydonk | 600/549 |
| 5,967,976 A | * | 10/1999 | Larsen et al. | 600/374 |
| 5,971,968 A | * | 10/1999 | Tu et al. | 604/264 |
| 6,004,319 A | * | 12/1999 | Goble et al. | 606/48 |
| 6,246,912 B1 | | 6/2001 | Sluijter et al. | |
| 6,285,903 B1 | * | 9/2001 | Rosenthal et al. | 600/433 |
| 6,514,249 B1 | * | 2/2003 | Maguire et al. | 606/41 |
| 6,602,242 B1 | | 8/2003 | Fung et al. | |
| 6,896,675 B2 | | 5/2005 | Leung et al. | |
| 7,306,596 B2 | | 12/2007 | Hillier et al. | |
| 7,337,005 B2 | | 2/2008 | Kim et al. | |
| 2004/0083002 A1 | | 4/2004 | Belef et al. | |
| 2004/0210290 A1 | | 10/2004 | Omar-Pasha | |
| 2006/0095059 A1 | | 5/2006 | Bleich et al. | |
| 2007/0287998 A1 | | 12/2007 | Sharareh et al. | |

FOREIGN PATENT DOCUMENTS

WO 88008610 11/1988

OTHER PUBLICATIONS

Sluijter, Menno; "Radiofrequency ablation in the management of spinal pain;" Contraversies and Consensus in Imaging and Intervention; Apr. 2006, vol. IV, Issue 1, pp. 10-15.
Cosman Medical; Cosman Spinal Electrode Kit; http:/lwww.cosmanmedical.com/Pages/csk.html.

* cited by examiner

*Primary Examiner* — Manuel Mendez
(74) *Attorney, Agent, or Firm* — Fish & Associates, PC (57) ABSTRACT

An integrated catheter shaft with a guidewire and a radio frequency wire is used in a catheter to deliver radio frequency energy to a treatment site. The small entry wound and the long integrated catheter shaft allows a user to thread the shaft along a tortuous route along a spinal canal to reach a treatment site while causing a minimal amount of trauma to the patient.

29 Claims, 6 Drawing Sheets

HIGH FREQUENCY EPIDURAL NEUROMODULATION CATHETER WITHOUT NEEDLE FOR EFFECTUATING RF TREATMENT

CROSS-REFERENCE TO RELATED APPLICATION

This application is a continuation-in-part of patent application Ser. No. 11/752,210, filed May 22, 2007, which claims priority to provisional application Ser. No. 60/802,685, filed on May 23, 2006, which are both hereby incorporated by reference in their entirety.

FIELD OF THE INVENTION

The field of the invention is pain treatment medical devices.

BACKGROUND OF THE INVENTION

Lower back pain is a common problem for many patients across the world. Frequently, lower back pain can not be fully treated, and can only be managed through pain therapy treatments such as medication or massage therapy. In more extreme situations, doctors can provide pain therapy by applying radiofrequency energy to the spine. U.S. Pat. No. 5,433,739 to Sluijter teaches a radiofrequency device that can be inserted into a spinal structure to heat and kill nerve structures and deliver pain relief. Unfortunately, such a technique can be indiscriminate in its destruction and can greatly harm the patient even if used by a skilled surgeon. Sluijter '739 and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

A further study, published in "Radiofrequency ablation in the management of spinal pain" ($C^2I^2$ Volume IV, Issue 1, pub. April 2006), has demonstrated that pulsed radiofrequency energy can be used to minimize the damage done to the spinal column and still be effective at treating pain. However, the current apparatus and method for delivering such radiofrequency energy uses a short, straight SMK disposable catheter which requires an operation to open a large wound around the area of the treatment site for the catheter. Not only can the patient become infected during such an operation, but some intervertebral discs may not have adequate space between them for the catheter to maneuver.

U.S. Pat. No. 6,602,242 to Fung teaches an electrode catheter that can be guided to send radiofrequency energy to a spinal nerve treatment site, however, such a large catheter also requires the medical professional to open a large wound in the patient's back for surgery before the catheter can be used. A larger wound exposes the patient to more surgical complications and extends the recovery time of patients from recovering from the ablation process.

Thus, there is still a need for improved systems and methods of delivering pulsed radiofrequency energy.

SUMMARY OF THE INVENTION

The present invention provides apparatus, systems and methods in which an integrated catheter with both a guidewire and a radio frequency wire percutaneously delivers radio frequency energy to a treatment site. The treatment site is generally located along the spinal of the patient, for example an epidural space in the lumbar region. Contemplated patients include any animal with a spine, for example canines, monkeys, or cats, but are preferably human beings.

The catheter preferably has a flexible shaft that is small enough to be used on a patient percutaneously. The shaft preferably has an outer diameter of at most than 3 mm, but is more preferably at most 2 mm, 1.5 mm, 1.2 mm, or even at most 1 mm in diameter. In an exemplary embodiment, the outer diameter of the shaft is at most 0.7 mm. As used herein, an "outer diameter" of the shaft is the distance between opposing exterior surfaces of the shaft. While the term "diameter" commonly refers to a circular cross-section, the cross-section of the catheter could be other shapes, for example ovals, squares, and triangles. Unless a contrary intent is apparent from the context, all ranges recited herein are inclusive of their endpoints, and open-ended ranges should be interpreted to include only commercially practical values.

As used herein, a "percutaneous" medical procedure is one where access to the inner organs of the patient is via a needle-sized puncture in the skin rather than by first opening a hole in the patient before inserting the needle. Generally, a needle or a cannula is first inserted into the epidural space, and the shaft of the catheter is then inserted into the needle and is then guided towards the treatment site. Needles could have an outer diameter as large as 6 mm, but are preferably at most 5 mm, 4.5 mm, 4 mm, 3.5 mm, or even at most 3 mm. A smaller needle reduces the size of the wound and minimizes the amount of pain and trauma caused to the patient during the procedure.

The shaft has a proximal end that is handled by a medical professional or a machine and a distal end that enters the patient and is guided towards the treatment site. The distal end could be a sharp tip, but is preferably blunt to reduce any trauma to the tissue surrounding the treatment site. A portion of the distal end is preferably made out of a material that transmits radio frequency energy and has a cross-section that forms an angled polygon. As used herein, an "angled polygon" is any polygon that is not an ellipse. An exemplary distal end is made of stainless steel and has a cross-section in the form of a teardrop to help focus radio frequency energy transmitted from the catheter to the treatment site.

The shaft itself is flexible enough to be guided through a tortuous path within the patient. A "tortuous path" is defined herein as any non-linear path that generally has at least two bends or turns. The shaft could be made of a flexible material, for example rubber or other polymers, or could be made of a stiff material that is segmented, for example stainless steel, to allow the shaft to bend in between the segments. While the segmented sections are preferably identical to one another and are evenly spaced apart, segmented sections could be evenly or unevenly spaced and could have segments of different dimensions without departing from the scope of the present invention.

The flexible shaft preferably also has a guidewire that is used to steer the catheter towards the treatment site. As used herein, a "guidewire" is any flexible wire, preferably metallic, that provides support to the structure of the shaft of the catheter. The guidewire could be embedded in a wall of the catheter, could be within a lumen of the shaft, or could compose the wall of the shaft itself. While the guidewire could extend along the entire length of the shaft, the guidewire is preferably at least 5, 10, or even 5 mm shorter than the length of the shaft, stopping just short of the distal end of the catheter. In this instance, and where other upper limits are not expressly stated, the reader should infer a reasonable upper limit. In this instance, for example, a commercially reasonable upper limit is about 30 mm. The guidewire could be guided and controlled using an electronic device connected to a proximal end of the catheter, but is preferably guided manually by pulling, pushing, and turning the proximal end of the catheter.

The tip of the distal end of the shaft preferably has an angulation to help with the steering. As used herein, an "angulation" is a stiff structure that rests at an angle from the rest of the shaft. The angulation is preferably malleable to allow a user to bend the tip of the distal end at a sharper or a gentler angle, depending on the needs of the user. By twisting and/or bending the angulation one way or another, a user could "aim" the shaft towards a treatment site before pushing the shaft forward, which helps guide the shaft along a tortuous path within the patient's body towards a treatment site. In an exemplary embodiment, the top of the distal end of the shaft has a larger diameter than the main body of the shaft, but is at most 1.5, 1.3, or even 1 mm in diameter.

The catheter also preferably has a radio frequency wire that is used to send radio frequency energy along the length of the shaft to the treatment site. It is contemplated that a user of the catheter could also transmit electrical current to the treatment site using the radio frequency wire. The radio frequency wire is preferably shorter than the shaft, and could be used to deliver radio frequency energy from any point of the catheter to any point along the shaft. Preferably, the radio frequency wire transmits radio frequency energy from the proximal end of the shaft to the distal tip of the shaft. A radio frequency adapter, for example a Radal™ adapter or a Tuohy-Borst™ adapter, could be used to couple the proximal end of the radio frequency wire to a radio frequency generator.

A radio frequency insulator preferably surrounds the radio frequency wire to prevent radio frequency energy from escaping the catheter shaft. Preferably, the radio frequency insulator encapsulates all but one or two sections of the radio frequency wire, although the radio frequency insulator could encapsulate the wire in a variety of ways without departing from the scope of the invention. The insulator could encapsulate just the wire, or could be embedded in the wall of the shaft itself. In an exemplary embodiment, the radio frequency insulator encapsulates all but the distal end of the shaft, allowing radio frequency energy to be transmitted only from the distal end of the shaft at a transmission site.

The transmission site could be the end of the radio frequency wire within the shaft, but is preferably the entire distal end of the shaft. The distal end of the shaft could be made of a material that easily transmits radio frequency energy, for example copper or platinum, such that when the radio frequency wire abuts the distal end of the shaft, the distal end of the shaft emits radio frequency energy. The distal end could be generally cylindrical in shape with a rounded end, which causes radio frequency energy to radiate evenly in all directions. It is contemplated, however, that radio frequency energy from the wire could be "aimed" by shaping the transmission site to have a cross section shaped like an angled polygon. As used herein, an "angled polygon" is any polygon that is not a circle or an ellipse that has at least one sharp angle. The transmission site could then be twisted to "aim" an angled protrusion of the transmission site, formed by the shape of the cross-section, towards the center of the treatment site to increase efficacy. While the cross section of the transmission site is preferably an angled polygon, the actual tip of the shaft is preferably blunt to prevent cutting, scraping, or otherwise causing unnecessary trauma to the treatment site.

The shaft also preferably has a temperature sensor that sends temperature readings to the proximal end of the catheter. The temperature sensor could detect a variety of temperatures along the length of the shaft, including for example the distal end of the shaft, the temperature of the patient at the treatment site, the temperature of the patient at a non-treatment site, or a combination thereof. In a preferred embodiment, the temperature sensor and the guidewire are the same wire to save space.

The temperature sensor and the radio frequency wire are preferably both attached to a common machine, so that the radio frequency energy that is sent can be regulated depending on temperature readings of the treatment site. For example, radio frequency energy could be streamed or pulsed towards the treatment site until a temperature has been reached, and then the radio frequency energy could be turned down or completely turned off until the temperature falls below a certain threshold. For example, a user who wishes to regulate a temperature of the treatment site to 40° F. could set the radio frequency energy to deactivate when the temperature is above 45° F. or even 42° F., and could set the radio frequency energy to reactivate when the temperature is below 35° F. or 38° F. The threshold temperatures could be set at any temperature without departing from the scope of the invention.

The catheter could also be used to inject medication into the treatment site by having a liquid passageway, for example a lumen, which extends along a length of the shaft. Preferably, the lumen has more than one injection ports at the distal end of the shaft to help distribute the medication evenly in multiple directions. The injection ports could be angled from one another, or could be parallel from one another, or be arranged in any variety of shapes without departing from the scope of the invention. The medication that is delivered to the treatment site could be any suitable liquid, for example a local anesthetic, a pharmaceutical, stem cells, proteins, or any other biological or genetically modified matter.

The catheter as described could easily be used to treat pain along a spine of an animal, preferably around the lumbar region. As used herein, "along the spine" means that a portion of the catheter is within 5 mm of a vertebra of the patient. In one embodiment, for example, a doctor could first insert a needle into an entry point of a human patient. Contemplated entry points include an epidural space, a paravertebral space, and a lumbar region, although the needle could be inserted in other points without departing from the scope of the current invention. The doctor could then thread the distal end of the catheter through the needle into the epidural space, and guide the tip of the catheter to a treatment site along the spine, for example the dorsal root ganglion, the spinal root, the spinal cord, or the epidural space itself. Preferably, the treatment site is by or between two vertebrae of the patient's spine. Preferably, the doctor steers the catheter shaft through a tortuous path by manipulating the proximal end of the catheter while following the shaft's movements through a fluoroscope. An angulation of the distal end could improve the accuracy of the procedure by helping the doctor steer the catheter through the tortuous path and aim radiofrequency energy and/or medication being delivered to the treatment site.

Once the distal end of the catheter shaft is guided to the treatment site, the doctor could then easily inject medication, extract tissue, send streams or pulses of radio frequency energy, and/or detect the temperature of the treatment site without needing to remove the catheter between tasks. The catheter itself could be made from reusable material so as to be easily sterilized for multiple uses, or could be made from cheaper, biodegradable material so as to be easily disposed of after a single use. Any suitable material for making catheters could be used without departing from the scope of the invention Various objects, features, aspects and advantages of the inventive subject matter will become more apparent from the following detailed description of preferred embodiments, along with the accompanying drawings in which like numerals represent like components.

DETAILED DESCRIPTION OF THE DRAWING

Figure 1:
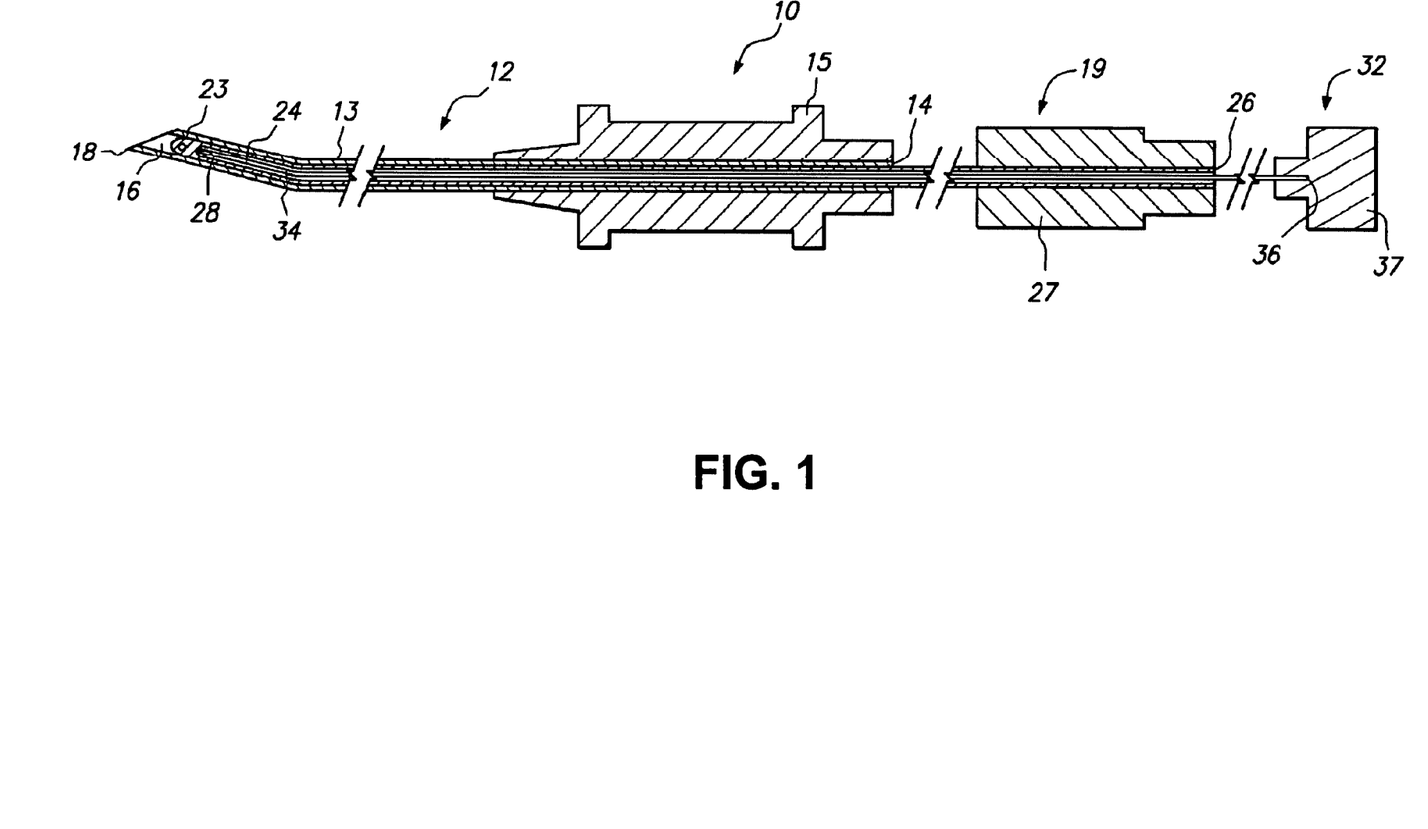
FIG. 1 is a partially exploded, cross-sectional view of a catheter apparatus constructed in accordance with the present invention.

Referring to the drawings to illustrated preferred embodiments, but not for the purpose of limiting the invention, FIG. 1 shows a partially assembled catheter apparatus 10 constructed in accordance with the present invention. The catheter apparatus 10 generally includes a needle assembly 12 having an elongate needle 13, a shaft assembly 19 having an elongate shaft 20, and a catheter hub 37. Needle 13 has an outer diameter of 4.5 mm, but could be larger or smaller depending on the needs of the operation and the thickness of shaft 20. Preferably, needle 13 has an outer diameter of at most 6 mm, and even more preferably at most 4 mm. Preferably, the outer diameter of shaft 20 and the inner diameter of the needle 13 (i.e., the diameter of the lumen 16) are sized relative to each other within a prescribed tolerance range to permit slidable movement of shaft 20 through lumen 16, yet presents a close enough fit to substantially inhibit fluid leakage therebetween.

Needle 13 of needle assembly 12 has an open proximal end 14 which is defined within one end of an enlarged needle hub 15 of needle assembly 12, where needle 13 is partially disposed within needle hub 15. Needle hub 15 is configured to be easily graspable to allow for the insertion of needle 13 into a desired entry point in the patient, preferably the epidural space. Needle 13 further includes a hollow lumen 16 and an open distal end 18. Hollow lumen 16 is generally shaped and sized to allow a catheter shaft of at most 1.3 mm in diameter to slide in and out of hollow lumen 16 without abrasive shearing. Preferably, the interior of hollow lumen 16 is padded around the open distal end 18 to further prevent sheering. The distal end 18 of needle 13 is itself defined by a sharpened tip for penetrating a patient's tissue, although other unsharpened tips could be used without departing from the scope of the invention. A sharpened tip is preferred as it allows a user to penetrate a spinal canal or an epidural space before guiding the catheter shaft to the treatment site (not shown). Needle assembly 12 could be manipulated (i.e., distal end 18 of needle 13 could be advanced through the patient's tissue to a desired treatment site with the spinal canal) by manually grasping the needle hub 15 thereof. It is also contemplated that a mechanical manipulator could be coupled to needle hub 15 to assist in manipulation of the needle assembly in the correct location of the patient.

Figure 2:
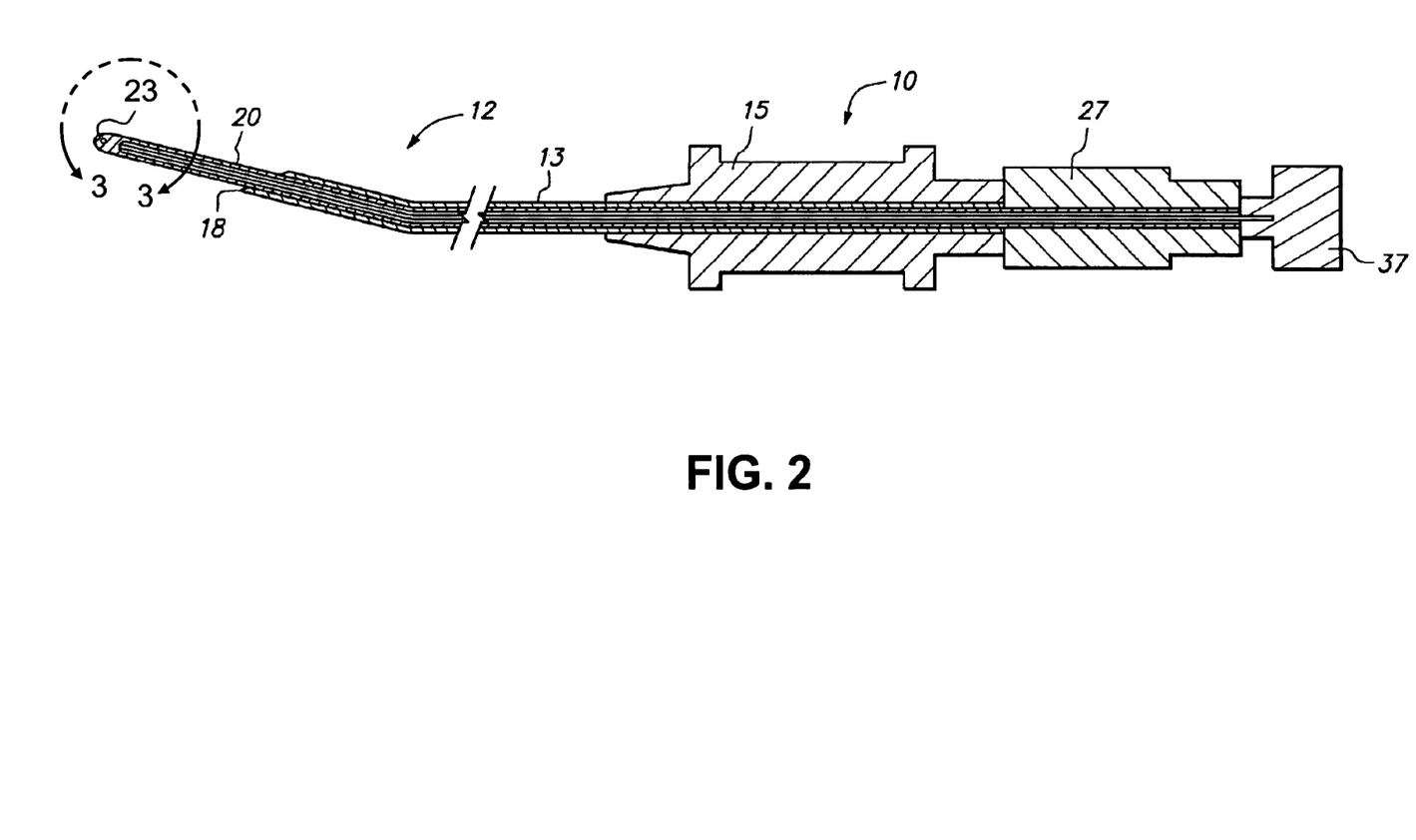
FIG. 2 is a cross-sectional view of the catheter apparatus shown in FIG. 1 in a fully assembled state.

Catheter apparatus 10 of the present invention further comprises a shaft assembly 19 which is cooperatively engageable to needle assembly 12 in the manner shown in FIGS. 1 and 2. While shaft assembly 19 is shown as being engageable to needle assembly 15, and preferably engages needle assembly 15 during use to prevent the catheter shaft from moving during treatment, shaft assembly 19 could freely move without attaching itself to needle assembly 15 during use. Shaft assembly 19 comprises an elongate, flexible shaft 20 which is telescopically disposed within and selectively advanceable through lumen 16 of needle 13. While shaft 20 is shown as a single, flexible material, shaft 20 could be made of a series of stiff segments coupled together on rotatable junctions to allow shaft 20 to appear flexible as a whole. Preferably, shaft 20 is made of stainless steel segments. Shaft 19 generally has an outer diameter of about 1.2 mm except for the distal tip, where the outer diameter widens to about 1.4 mm, but shaft 19 could have larger or smaller dimensions without departing from the scope of the current invention.

Shaft 20 includes a closed distal end 23 which is itself defined by a blunt tip having a generally semi-spherical outer surface. Preferably, distal end 23 has an angulation that could be reshaped to allow for an angled distal tip. While the surface of the distal tip is generally semi-spherical, the cross-section of the tip could be angled in various ways. In addition to the distal end 23, shaft 20 further comprises three lumens 24 that lead to proximal end 26. While all hollow lumens 24 lead to the same proximal end, hollow lumens 24 could be of different lengths and could have multiple proximal ends along the length of the needle assembly without departing from the scope of the invention. Proximal end 26 of shaft 20 is defined within an enlarged catheter hub 27 of shaft assembly 19 such that shaft 20 is partially disposed within catheter hub 27.

As shown in FIG. 2, when shaft assembly 19 is connected to needle apparatus 10, the length of shaft 20 exceeds the length of needle 13 such that when shaft assembly 19 is operatively coupled to the needle assembly 12 (i.e., the catheter hub 27 engages the needle hub 15), distal portion 23 of shaft 20 will protrude well beyond distal end 18 of needle 13. While the current embodiment shows the catheter protruding only 10 mm past the end of the needle, it is contemplated that the catheter could protrude at least 20 mm, 40 mm, or even 80 mm beyond the end of the needle as it threads through a tortuous path to the treatment site.

Figure 3:
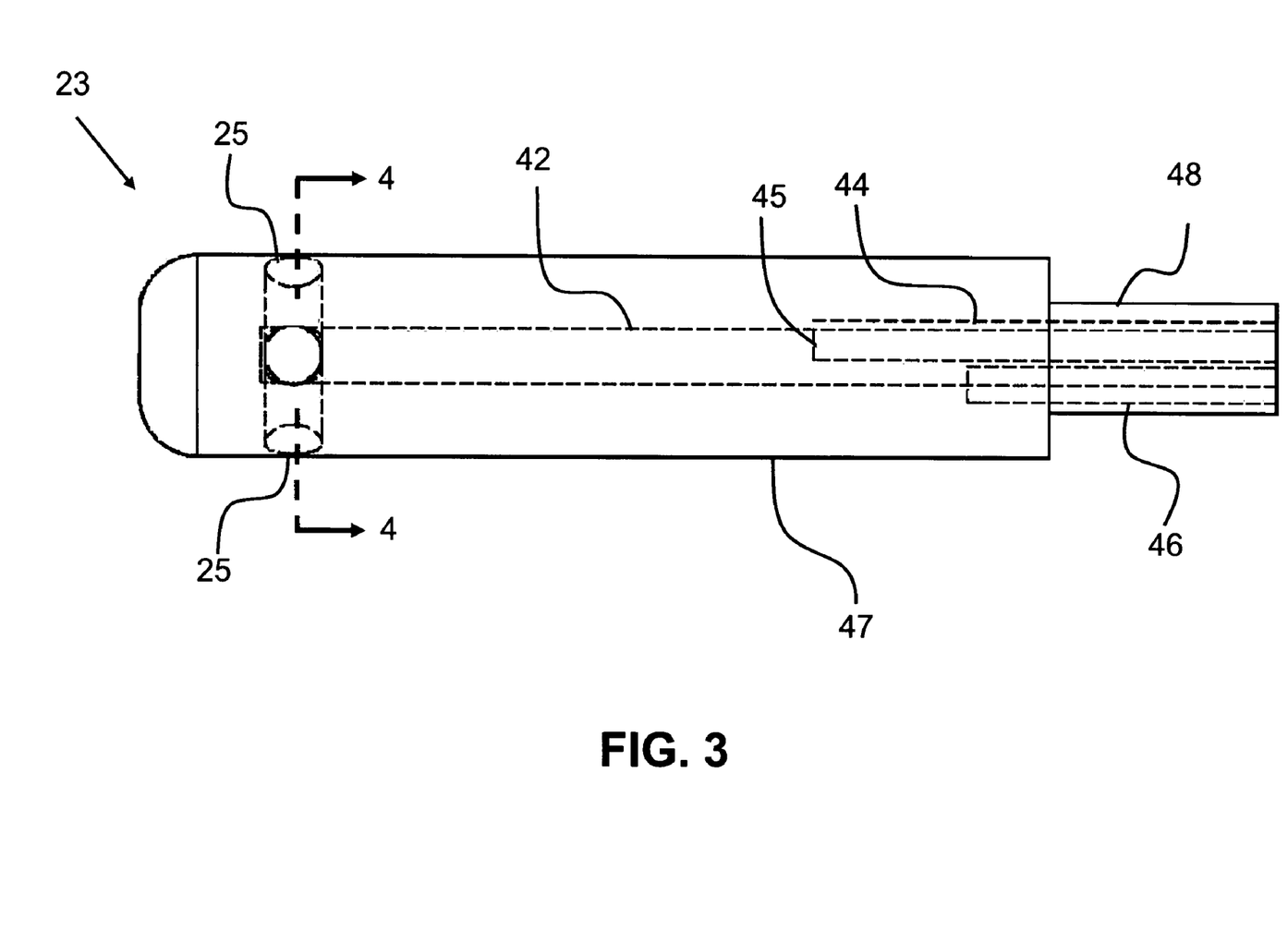
FIG. 3 is an enlargement of the encircled region 3-3 shown in FIG. 2.

A close up of distal end 23 is shown in FIG. 3, which has three lumens: fluid passageway 42 that leads to injection ports 25; radio frequency wire 44, and temperature sensor wire 46 that all terminate within angulation 47. Angulation 47 is preferably made from a single stiff yet malleable material that conducts both radiofrequency energy and electrical current, although the material could be made of non-conductive materials without departing from the scope of the invention. Preferably, angulation 47 is bendable only along a single joint (not shown) so that the angulation could be bent and/or twisted in various directions without collapsing or deforming the lumens within, thereby preserving the overall function of catheter 10. Since radio frequency wire 44 abuts angulation 47, angulation 47 acts as a transmission site for any radio frequency energy or electrical energy that is sent along the radio frequency wire. A user could angle the angulation with respect to the rest of the catheter shaft, helping to aim the transmitted energy and also to steer the catheter shaft to the treatment site.

Figure 4:
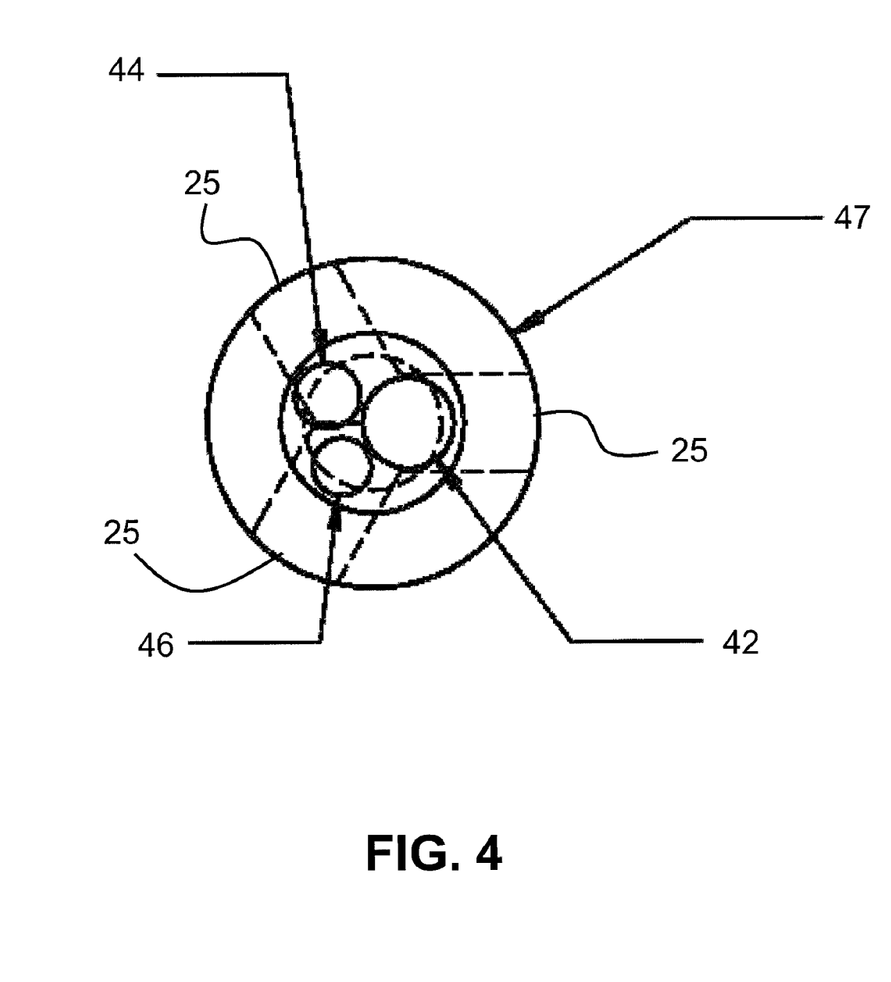
FIG. 4 is a cross-sectional area of the catheter shaft shown in FIG. 3 taken along line 4-4.

Fluid passageway 42 leads to multiple injection ports 25, better seen in cross-section FIG. 4 as three injection ports 25 that equally distribute medication in three directions, approximately 120 degrees apart from one another. While the injection ports are shown as three equally spaced injection ports along a single cross-section, more or less injection ports could be used at varying angles that could be distributed across the entire length of distal end 23. The injection ports are preferably located on the side wall of distal end 23, as opposed to the tip of the distal end, in order to minimize the amount of tissue that may plug up the injection port.

Radio frequency wire 44 is constructed from a flexible material, preferably metal, that is capable of transmitting radio frequency energy. Preferably, radio frequency wire 44 also transmits electrical energy. Shaft 20 is encapsulated is covered or encapsulated by an insulating layer 48 of material that insulates against both electrical energy and radio frequency energy. Suitable materials are disclosed in WO/1988/008610, which is incorporated herein by reference in its entirety. As shown in FIG. 3, angulation 47 is not covered by insulating layer 48, which allows radio frequency and/or electrical energy of being freely transmitted from angulation 47. It is contemplated that other kinds of energy could be sent through radio frequency wire 44, for example electrical energy, ultrasound energy, acoustical energy, optical energy, and optics acoustical energy.

Temperature sensor 46 is also constructed from a flexible material that is capable of detecting temperature and changes in temperature. Temperature sensor 46 is configured to detect the temperature of angulation 47, but could also be threaded through a hole in the angulation or in the wall of the catheter itself to detect a temperature of the surrounding tissue. All suitable temperature sensor materials could be used without departing from the scope of the current invention. In the current embodiment, temperature sensor 46 is made from a robust, flexible material that provides form to the catheter so that it also acts as a guidewire for shaft 20. It is contemplated that temperature sensor 46 could be replaced by other sensors, for example an electrical sensor, an ultrasound sensor, an acoustics sensor, an optics sensor, and an optic acoustics sensor.

A radio frequency adapter 32 is cooperatively engageable to shaft assembly 19, and could be connected to a radio frequency or an electrical current generator, for example COSMAN™, STRIKER™, SMITH NEPTHER™, BALLARD™, and KIMBERLY CLARK™ radio frequency generators. Contemplated radio frequency adapters include radal adapters and tuohy-borst adapters. The radio frequency adapter 32 generally comprises the radio frequency wire 44, which is capable of conveying or transmitting radio frequency energy or electrical energy received from a generator (not shown). Radio frequency wire 44 has a distal end 45 and an opposed proximal end 36 which resides within an adapter hub 37 of the radio frequency adapter 32. The adapter hub 37 is itself configured to be operatively coupled to the radio frequency generator in a manner which effectively facilitates the transmission of radio frequency energy from the radio frequency generator into the radio frequency wire 44, and finally into angulation 47. Preferably, the radio frequency adapter 32 is configured to couple with both the radio frequency wire 44, and the temperature sensor 46 so that a single machine could automatically deliver bursts of radio frequency energy based upon sensed temperature.

Figure 5A:
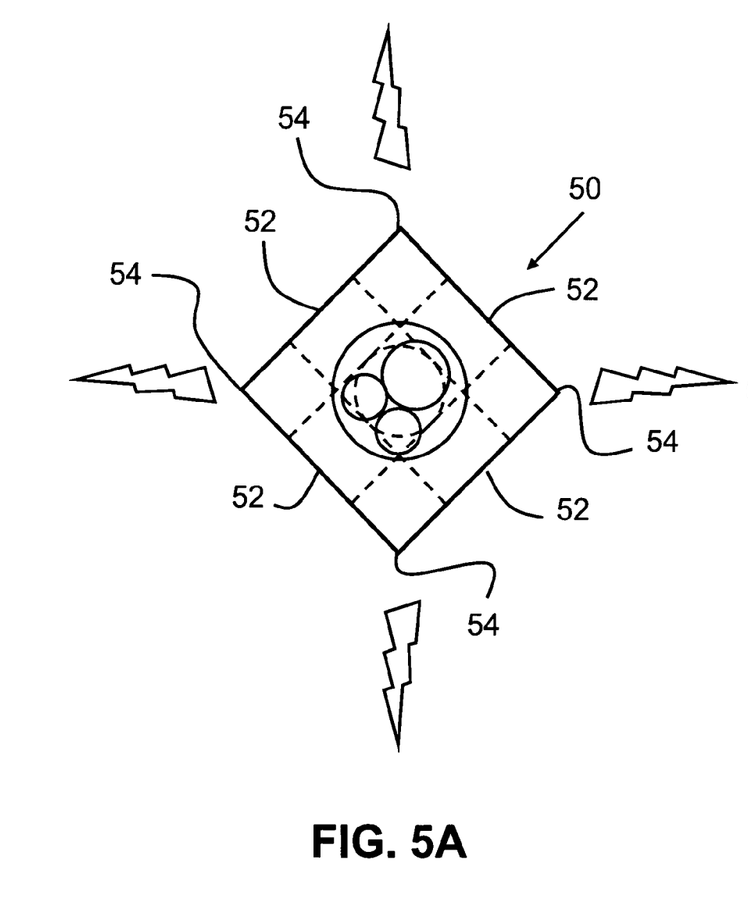
FIGS. 5A and 5B show alternative embodiments of cross-sectional areas of contemplated catheters.
Figure 5B:
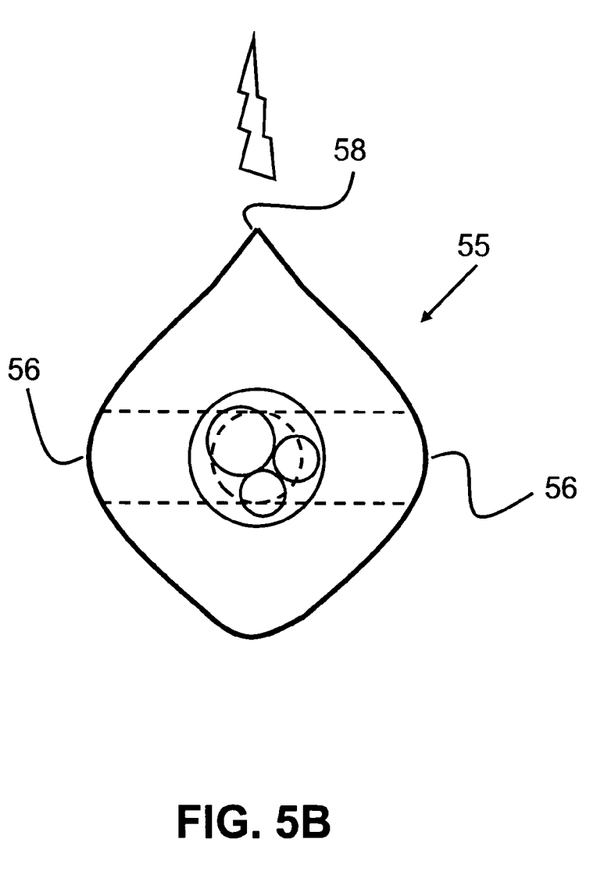

Radio frequency energy could be "aimed" at a treatment site by shaping the angulation (or the radio frequency wire itself in cases where the angulation does not transmit radio frequency energy) as an angled polygon. FIGS. 5A and 5B show alternative cross sections 50 and 55 with a square angled polygon and a teardrop angled polygon. Cross section 50 has four injection ports 52 that evenly disperse medication in four opposing directions, and has four angled projections 54 that focus radio frequency energy towards the tip of the angled projection. A doctor who wishes to transmit radio frequency energy in a square-shaped pattern could use an angulation with a square-shaped cross-section. A preferred cross-section is the teardrop angled polygon shown in cross-section 55. Teardrop angled polygon has two injection ports 56, but only one angled projection 58. Radio frequency energy will be concentrated at the tip of angled projection 58, and the doctor could twist and turn the angled projection to focus the intensity of the radio frequency towards a specific trouble spot. An exemplary angulation tapers from the angled cross-section towards a spherical shape near the distal end of the angulation, so as to provide a blunt distal tip for the catheter.

Since distal portion 23 of shaft 20 could protrude from the distal end 18 of needle 13, the blunt distal end 23 of the shaft 20 could be guided to a desired treatment region within or just outside of the spinal canal of the patient. Such positioning or placement may be effectuated without causing sheering damage to the treatment region due to the absence of any sharpened point or tip on the distal portion 23 of the shaft 20. The positioning of the distal end 23 of the shaft 20 at the appropriate treatment site treatment site could be facilitated by the selective manipulation of the catheter hub 27 of the shaft assembly 19 manually or with the assistance of a machine. Preferably, the catheter is guided to the treatment site under the guidance of a fluoroscope or another similar X-ray device.

Figure 6:
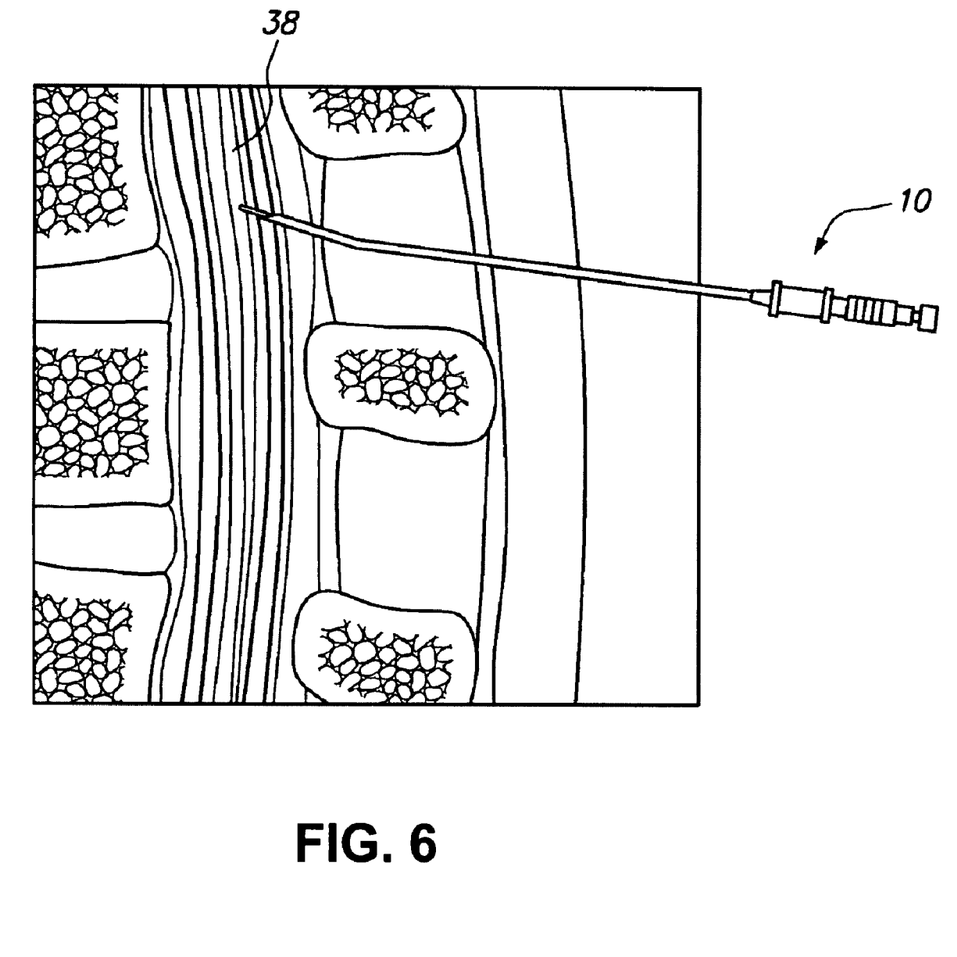
FIG. 6 is a side cross-sectional view of the catheter apparatus of FIG. 1 being used on a patient's lumbar area.

In FIG. 6, catheter apparatus 10 is used to deliver medication and radio frequency energy to dorsal nerve 38. Prior to guiding the catheter shaft to the treatment site, the shaft could first be pulled back into needle 13 of needle assembly 12 so that the distal end 23 of shaft 20 does not protrude beyond the distal end 18 of needle 13. Since distal end 23 does not protrude beyond sharpened distal end 18, the user of the catheter apparatus 10 is able to use the sharpened distal end 18 of the needle 13 to pierce or penetrate the patient's tissue to an appropriate entry site, preferably adjacent to the desired treatment site. After needle 13 has penetrated the patient's tissue, shaft 20 could be advanced through lumen 24 of needle 13, and guided to the treatment site. While FIG. 6 shows the catheter shaft being advanced only a few millimeters to reach the treatment site, a skilled physician with a longer shaft could thread the shaft up through the entire spinal canal to hit a vertebra more than 40 mm from the entry point.

Again, imaging techniques, including x-ray imaging, could be used to visually assist the user in properly placing or positioning distal end 23 of shaft 20 at the desired treatment site 38 within the patient's spinal canal. Once the distal end 23 of shaft 20 has been properly positioned at the desired treatment region within the spinal canal 38 of the patient, the user could then inject medication, apply electronic current to the treatment site, and/or could apply radio frequency energy to the treatment site. Upon the completion of the treatment, the catheter apparatus 10 is simply withdrawn from within the spinal canal 38 of the patient.

Advantageously, because the distal end 23 of the shaft 20 has a closed, blunt configuration, critical treatment areas within the spinal canal 38 of the patient may be reached with substantially reduced risk of permanently damaging the nerves to be treated as could occur by any attempted placement of the sharpened tip of a needle near such nerves. In this regard, sharpened distal end 18 of needle 13 need not be placed in close proximity to the treatment region within the spinal canal 38 of the patient due to the capability of advancing the distal portion 23 of the shaft 20 substantially beyond distal end 18 through the use of shaft assembly 19 of the present invention, especially with extra-long catheter shafts with integrated guidewires. Additionally, since the catheter shaft has the combined functionality of a guidewire, an injection lumen, a radio frequency transmitter, an electrical energy transmitter, and a temperature sensor, multiple wires do not need to be threaded through the same lumen over and over again, which reduces trauma to the patient and possible shearing within the lumen. Thus, due to its structural and functional attributes, the catheter apparatus 10 of the present invention is capable of being used in critical treatment areas within the spinal canal 38 of a patient while minimizing trauma to the patient.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A guideable catheter for delivering radiofrequency energy to a treatment site; comprising:
   a flexible shaft having a proximal end and a distal end;
   a radio frequency open-circuit wire having a transmission site, wherein the wire extends along a first length of the shaft to the distal end of the shaft; and
   a radiofrequency adapter that couples a radiofrequency transmitter to the radio frequency wire, wherein a cross-section of the radio frequency wire's transmission site has a tip where the point of the tip forms an angle that aims radio frequency energy from the radiofrequency transmitter through the tip to increase a temperature of the treatment site.

2. The catheter of claim 1, wherein the outer diameter of the shaft is at most 2 mm.

3. The catheter of claim 1, wherein the outer diameter of the shaft is at most 1 mm.

4. The catheter of claim 1, wherein the distal end of the shaft comprises an angulation.

5. The catheter of claim 1, further comprising a radio frequency insulator at least partially encapsulating the radio frequency wire.

6. The catheter of claim 5, wherein the radio frequency insulator encapsulates all but a distal end of the radio frequency wire.

7. The catheter of claim 1, further comprising a radio frequency adapter coupled to a proximal end of the radio frequency wire.

8. The catheter of claim 7, wherein the adapter is selected from the group consisting of a radal adapter and a tuohy-borst adapter.

9. The catheter of claim 7, wherein the radio frequency adapter transmits pulses of radiofrequency energy to the radiofrequency wire.

10. The catheter of claim 7, wherein the radio frequency adapter transmits an electrical current to the radiofrequency wire.

11. The catheter of claim 1, further comprising a fluid passageway within the shaft concurrently extending along a second length of the shaft to an injection port at the distal end of the shaft.

12. The catheter of claim 11, wherein the fluid passageway extends to a second injection port at the distal end of the shaft.

13. The catheter of claim 11, further comprising a guidewire concurrently extending along a third length of the shaft.

14. The catheter of claim 11, wherein the fluid passageway accepts medication to flow out of the injection port.

15. The catheter of claim 1, further comprising a temperature sensor extending along a fourth length of the shaft.

16. The catheter of claim 15, further comprising a machine coupled to the temperature sensor and the radiofrequency wire that stops transmission of radiofrequency energy to the radiofrequency wire when a temperature detected by the temperature sensor rises above a first threshold temperature.

17. The catheter of claim 16, wherein the first threshold temperature is 42° F.

18. The catheter of claim 16, wherein the machine resumes transmission of radiofrequency energy to the radiofrequency wire when the temperature falls below a second threshold temperature.

19. The catheter of claim 18, wherein the second threshold temperature is 38° F.

20. The catheter of claim 1, wherein the distal end of the shaft is blunt.

21. The catheter of claim 1, wherein a cross-section of the distal end of the shaft is an angled polygon.

22. The catheter of claim 21, wherein the angled projection forms an edge from the cross-section of the distal end to a blunt tip of the distal end.

23. The catheter of claim 21, wherein the distal end tapers from the cross-section having the angled polygon to a cross-section having spherical shape.

24. The catheter of claim 1, wherein a cross-section of the distal end of the shaft is tear-shaped.

25. The catheter of claim 1, wherein the catheter comprises stainless steel.

26. The catheter of claim 1, further comprising a guidewire concurrently extending along a second length of the shaft.

27. The catheter of claim 1, wherein the guidewire is a temperature sensor.

28. The catheter of claim 1, wherein the angle of the point of the tip is formed by a pair of flat walls.

29. The catheter of claim 1, wherein the angle of the point of the tip is formed by a pair of concave walls.

* * * * *